United States Patent [19]  
Langlois

[11] 4,403,508  
[45] Sep. 13, 1983

[54] LOCATING INTERFACES IN VERTICALLY-LAYERED MATERIALS AND DETERMINING CONCENTRATIONS IN MIXED MATERIALS UTILIZING ACOUSTIC IMPEDANCE MEASUREMENTS

[75] Inventor: Gary N. Langlois, Richland, Wash.

[73] Assignee: The United States of America as represented by the U.S. Department of Energy, Washington, D.C.

[21] Appl. No.: 272,227

[22] Filed: Jun. 10, 1981

[51] Int. Cl.³ .................. G01N 29/02; G01F 23/28
[52] U.S. Cl. ........................... 73/589; 73/290 V
[58] Field of Search ............ 73/574, 589, 599, 290 V; 340/621

[56] References Cited

U.S. PATENT DOCUMENTS

| | | | |
|---|---|---|---|
| 3,520,186 | 7/1970 | Adams et al. | 73/290 V |
| 3,656,134 | 4/1972 | Brown | 340/621 |
| 3,695,108 | 10/1972 | Wygant | 73/290 R |
| 3,791,200 | 2/1974 | Hayre | 73/589 |
| 3,883,841 | 5/1975 | Norel et al. | 73/589 |
| 3,889,523 | 6/1975 | Nolte | 73/290 V X |
| 4,118,983 | 10/1978 | Brazhnikov | 73/290 V X |
| 4,203,324 | 5/1980 | Baumoel | 73/290 V |
| 4,320,659 | 3/1982 | Lynnworth et al. | 73/589 |

FOREIGN PATENT DOCUMENTS 720970 11/1965 Canada .................. 340/621

OTHER PUBLICATIONS

"Ultrasonic Methods of Testing Materials" by Filipczynski et al. London, Butterworth's 1966, p. 83.
"Ultrasonic Testing of Materials" by Krautkramer, New York, Springer-Verlag, 1969, pp. 16-23.

*Primary Examiner*—James J. Gill
*Attorney, Agent, or Firm*—Robert Southworth, III; Richard E. Constant; Richard G. Besha

[57] ABSTRACT

Measurement of the relative and actual value of acoustic characteristic impedances of an unknown substance, location of the interfaces of vertically-layered materials, and the determination of the concentration of a first material mixed in a second material. A highly damped ultrasonic pulse is transmitted into one side of a reference plate, such as a tank wall, where the other side of the reference plate is in physical contact with the medium to be measured. The amplitude of a return signal, which is the reflection of the transmitted pulse from the interface between the other side of the reference plate and the medium, is measured. The amplitude value indicates the acoustic characteristic impedance of the substance relative to that of the reference plate or relative to that of other tested materials. Discontinuities in amplitude with repeated measurements for various heights indicate the location of interfaces in vertically-layered materials. Standardization techniques permit the relative acoustic characteristic impedance of a substance to be converted to an actual value. Calibration techniques for mixtures permit the amplitude to be converted to the concentration of a first material mixed in a second material.

2 Claims, 6 Drawing Figures

LOCATING INTERFACES IN VERTICALLY-LAYERED MATERIALS AND DETERMINING CONCENTRATIONS IN MIXED MATERIALS UTILIZING ACOUSTIC IMPEDANCE MEASUREMENTS

The U.S. Government has rights in this invention pursuant to Contract No. DE-AC06-77RL01030 between the U.S. Department of Energy and the Rockwell International Corporation.

BACKGROUND OF THE INVENTION

The present invention relates generally to soundwave probes and more particularly to a soundwave method and device adaptable to measure, for solids, liquids and/or gases, the acoustic characteristic impedance of a medium, the interfaces of vertically-layered materials defining a medium, and the concentration in a medium of a first material mixed in a second material.

It is well known in the art of soundwaves that all materials have an acoustic characteristic impedance which is the product of the density of the material and the acoustic velocity through the material. Known techniques for calculating the acoustic characteristic impedance include separate measurements of the density and velocity. A known method for measuring the velocity, said to be limited to materials such as rubbers and plastics immersed in water, utilizes the reflection of ultrasonic pulses incident normally to a boundary between two media (Filipczynski, L. et al., *Ultrasonic Methods of Testing Materials.* London, Butterworth's, 1966. p. 83).

Direct measurement of acoustic characteristic impedance has been made in liquid by compensating the damped capacitance of the transmitting transducer with the inductive reactance and measuring the voltage across the transmitting transducer, which will vary with the acoustic impedance at resonance. This known method is limited in dynamic range, and must be in direct contact with the liquid it is measuring. It is more suitable for a laboratory environment.

Also known in the art are ultrasonic transmission liquid level detectors that relay on attenuation and/or velocity between a transmitter and a receiver to locate or control the interface. These devices require direct contact with the vessel contents and can be limited by environmental considerations.

Additionally known in the art are pulse echo methods where the elapsed time from transmission to the reflected signal from the interface determines the location of the interface. These devices also require direct contact with the vessel contents, where environmental conditions as well as interface disturbances can limit their usefulness.

Likewise known in the art is a method for generating lamb waves in a vessel wall and monitoring the received acoustic wave at a separate location. The vessel contents will dampen the lamb waves and from this an interface in the vessel contents can be determined (U.S. Pat. No. 4,118,983, Brazhnikov, 1978). Though this system has none of the drawbacks of systems that must be introduced into direct contact with the vessel contents, the orientation, frequency, wave shape and band pass that must be controlled for the method to work properly make it excessively complex.

SUMMARY OF THE INVENTION

It is an object of this invention to provide a method for accurately measuring the acoustic characteristic impedance of a material.

It is another object of the invention to provide a simple method for measuring a vertically-layered gas/liquid, liquid/solid or other interface within a vessel with or without directly contacting the vessel contents.

It is a further object of the invention to provide a simple method for measuring the concentration of an electrolytic aqueous solution or other medium having one material mixed in a second material within a vessel with or without directly contacting the vessel contents.

It is also an object of the invention to measure the interstitial liquid level in buried nuclear waste tanks.

Additional objects, advantages, and novel features of the invention will be set forth in part in the description which follows, and in part will become apparent to those skilled in the art upon examination of the following or may be learned by practice of the invention. The objects and advantages of the invention may be realized and attained by means of the instrumentalities and combinations particularly pointed out in the appended claims.

To achieve the foregoing and other objects and in accordance with the purpose of the present invention, as embodied and broadly described herein, the method of measuring the relative acoustic characteristic impedance of a material may comprise placing a transmitter's highly damped soundwave transducer and a receiver's soundwave transducer against one side of a reference plate and positioning them so that the receiver's transducer can pick up the reflection of the transmitter's signal from the other side of the plate, placing the other side of the plate against the material, sending a highly damped soundwave pulse to, and receiving a return pulse from, the boundary between the other side of the plate and the material, and measuring the amplitude of the return pulse which is a measure of the material's relative acoustic characteristic impedance.

A method of measuring the actual value of acoustic characteristic impedance of a material may comprise measuring the relative acoustic characteristic impedance, as given above, and then calibrating the relative value to obtain the actual value.

The method of locating the boundaries of vertically-layered materials may comprise measuring the relative acoustic characteristic impedance, as given above, making additional measurements for various vertical heights and identifying the breaks in the amplitudes which indicate the locations of the boundaries.

The method of measuring the concentration of a first material mixed in a second material may comprise measuring the relative acoustic characteristic impedance, as given above, and then standardizing the amplitude to obtain the concentration.

The device for measuring the relative acoustic characteristic impedance of a material may comprise a reference plate having one side placed against a receiver's soundwave transducer and a transmitter's highly damped pulsed soundwave transducer. The receiver's transducer and the transmitter's transducer are positioned so that the receiver can pick up the reflection of the transmitter's signal from the other side of the plate which is placed against the material. An electronic gate passes mostly only the reflection to the receiver's amplifier. A measuring apparatus measures the amplitude of the reflection which is a measure of the relative acoustic characteristic impedance of the material.

The device for measuring the actual value of acoustic characteristic impedance of a material may comprise the device for measuring the relative acoustic characteristic impedance of a material, as given above, plus apparatus to calibrate the relative value to obtain the actual value.

The device for locating the boundaries of vertically-layered materials may comprise the device for measuring the relative acoustic characteristic impedance, as given above, apparatus for vertically moving the transmitter's transducer and the receiver's transducer, apparatus for measuring the vertical height of the transmitter and receiver transducers, and apparatus for detecting the breaks in the amplitudes for repeated measurements which indicate the locations of the boundaries.

The device for measuring the concentration of a first material mixed in a second material may comprise the device for measuring the relative acoustic characteristic impedance, as given above, plus apparatus to standardize the amplitude to obtain the concentration.

Several benefits and advantages are derived from the invention. Acoustic characteristic impedance, interface location, and concentration measurements can be easily made of a medium contained in a vessel with or without directly contacting the vessel contents. Also, the interstitial liquid level in buried nuclear waste tanks can be accurately determined.

BRIEF DESCRIPTION OF THE DRAWINGS

The accompanying drawings which are incorporated in and form a part of this specification, illustrate several embodiments of the present invention and, together with a description, serve to explain the principles of the invention. In the drawings.

DETAILED DESCRIPTION OF THE INVENTION

Reference will now be made in detail to several present preferred embodiments of the invention, examples of which are illustrated in the accompanying drawings.

Figure 1:
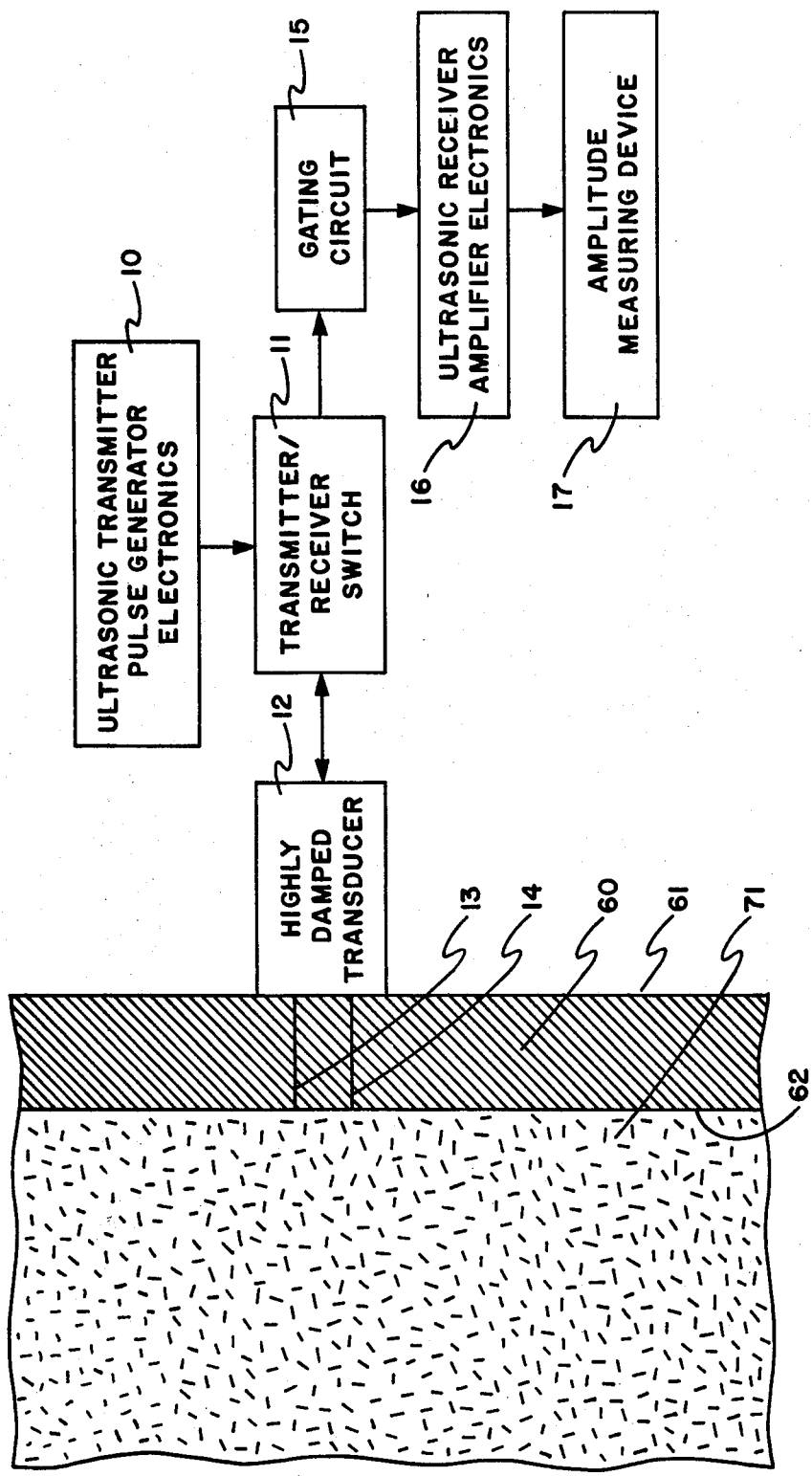
FIG. 1 is a block diagram of the device for measuring the relative acoustic characteristic impedance.

FIG. 1 depicts the basic configuration of the invention which is used to measure the relative acoustic characteristic impedance of a medium. FIG. 1 shows the medium as a salt 71, but the material to be measured could be any solid, liquid or gas. Specific acoustic impedance in soundwaves describes the resistance of a material to plane progressive waves and is considered a complex quantity. However, when the soundwave source is a highly damped pulse propagated through a thickness of a sufficient number of wavelengths, the imaginary component is minimized, and the real quantity left is primarily the product of the density and the velocity of sound and is called the acoustic characteristic impedance. This impedance for a given material is dependent only on its physical properties. All materials have an acoustic characteristic impedance. Low pressure gases have an acoustic characteristic impedance of essentially zero.

The invention's basic configuration of FIG. 1 will measure a relative value of the acoustic characteristic impedance quantity. The invention includes a highly damped pulsed ultrasonic transmitter which has ultrasonic transmitter pulse generator electronics 10, the transmitter setting of a transmitter/receiver switch 11 and a highly damped transducer 12. The transducer 12 may have a damping element, such as powdered metal-filled epoxy, bonded to a piezoelectric element. The transducer 12 is placed in acoustic contact with one side 61 of a reference plate 60. The reference plate 60 may be a vessel wall containing material to be measured, the wall of a drywell (closed-bottom tube) in a vessel containing the material to be measured, or a piece of a solid substance, having generally two opposing parallel sides, which will be placed in a container holding the material to be measured. If the reference plate were very thick (such as the wall of a rock cavern) a lower frequency non-ultrasonic soundwave would be used, as is appreciated by those skilled in the art.

The invention also includes an ultrasonic receiver which has ultrasonic receiver amplifier electronics 16, and for the particular arrangement of FIG. 1, the receiver setting of the transmitter/receiver switch 11 and the same highly damped transducer 12. The receiver could instead have a separate transducer which is placed in acoustic contact with the same side 61 of the reference plate 60 as was done with the transmitter's transducer. The other side 62 of the reference plate 60 is placed in intimate physical contact with the medium 71 to be tested. The transmitter's transducer and the receiver's transducer, or the common transducer 12 if shared by the transmitter and receiver, must be orientated such that the transmitter can transmit a pulse signal along a path 13 to the boundary or interface between the other side 62 of the reference plate 60 and the medium 71, and such that the receiver can receive the return signal pulse along a path 14 which is the reflection of the transmitted pulse from the same interface. This orientation is generally simple. Highly accurate pointing or exact positioning is not required as long as any subsequent measurements have the same orientation. In the case of the common transducer 12, its piezoelectric element is merely placed flat against the one side 61 of the reference plate 60 with a thin layer of appropriate acoustic couplant placed in between.

Electronic gating means are used before the receiver electronics 16 such that the receiver receives substantially only the return pulse signal. This noise filtering device provides a time window for the receiver and preferably includes a gating circuit 15. The gating circuit 15 is opened generally at the time the return pulse is expected to be received. The gate stays open generally for the expected duration of the return pulse and then closes. Thus, the receiver electronics 16 are shielded from false returns such as imperfections in the reference plate 60 itself or additional returns from beyond the interface. The time the return pulse is expected to be received may be determined several ways. One method is to know or measure the velocity of sound in the reference plate 60, together with its thickness, and simply divide twice the thickness by the velocity. Another method is to experimentally pick out and time the return signal from the interface, which is a simple technique for those skilled in the art.

The invention includes means for measuring the amplitude of the return pulse signal from the receiver electronics 16. Preferably this amplitude measuring device 17 is a typical circuit, known to those skilled in the art, which will measure the voltage level of the return pulse. This amplitude or voltage level indicates the relative acoustic characteristic impedance of the medium 71 at the point where the transmitted pulse encountered the interface between the medium 71 and the other side 62 of the reference plate 60. A voltage level of the return pulse having the same polarity as the transmitted pulse means the medium 71 has a greater acoustic characteristic impedance than that of the reference plate 60. A zero value of the return pulse means the medium 71 and reference plate 60 have the same value of the acoustic characteristic impedance. A return pulse of reverse polarity relative to the transmitted pulse means the medium 71 has a smaller acoustic characteristic impedance than that of the reference plate 60. If measurements are made on two media, the medium having an amplitude value more polarized towards the transmitted pulse's polarity has the greater acoustic characteristic impedance. For example, if the transmitted pulse has a positive polarity, the medium having the more positive value of the amplitude of the return signal will have the greater acoustic characteristic impedance relative to the other medium.

Several factors must be optimized to achieve the best results in making any acoustic characteristic impedance measurement. Preferably the transducer 12 should be made of a low Q piezoelectric material (e.g., lead meta niobate), be highly dampled by some backing material (e.g., a powdered metal-filled epoxy), and have a piezoelectric element thickness that is a small fraction of the round trip distance in the reference plate 60. It is better that the reference plate 60 be made of a homogeneous material with an acoustic characteristic impedance outside the range of acoustic characteristic impedance expected in the measurement to be performed, but within 10-25% of either extreme, and that the reference plate 60 have a thickness which is at least ten times greater than one half wavelength at the resonant frequency of the transducer 12 in the reference plate material. It is also preferred that the ultrasonic transmitter pulse generator electronics 10 be capable of generating a very fast rise time, narrow, high energy pulse for "shocking" the piezoelectric element into generating a sonic pulse, and be capable of operating at a repetition frequency such that each successive acoustic pulse is able to damp out before a new pulse is generated.

The operation of the basic configuration of the invention to measure relative acoustic characteristic impedance is as follows. The transmitting and receiving transducers, or the common transducer 12, are acoustically coupled to one side 61 of the reference plate 60 and orientated to receive the reflection of a transmitted pulse from the interface between the medium 71 and the other side 62 of the reference plate 60. Acoustic contact may be made by bonding or pressing the transducer 12 to the reference plate 60 using a couplant placed in between, preferably having a thickness less than 1/20 the wavelength of the resonant frequency of the piezoelectric element. The gating circuit 15 is set, as previously described, to pass substantially only the reflection to the receiver electronics 16. The other side 62 of the reference plate 60 is placed in contact with the medium 71 (if the reference plate is a vessel wall containing the medium, this placement is already accomplished). A narrow highly damped ultrasonic pulse is transmitted. When it reaches the boundary formed by the other side 62 of the reference plate 60 and the medium 71, a percentage of the signal is transmitted through the medium and a percentage is reflected back to the receiver. The amplitude measuring device 17 gives the amplitude of the reflection, which is a measure of the relative acoustic characteristic impedance of the medium 71, which is defined to be the acoustic characteristic impedance of the medium 71 relative to that of the reference plate 60 or relative to that of another tested medium.

Figure 2:
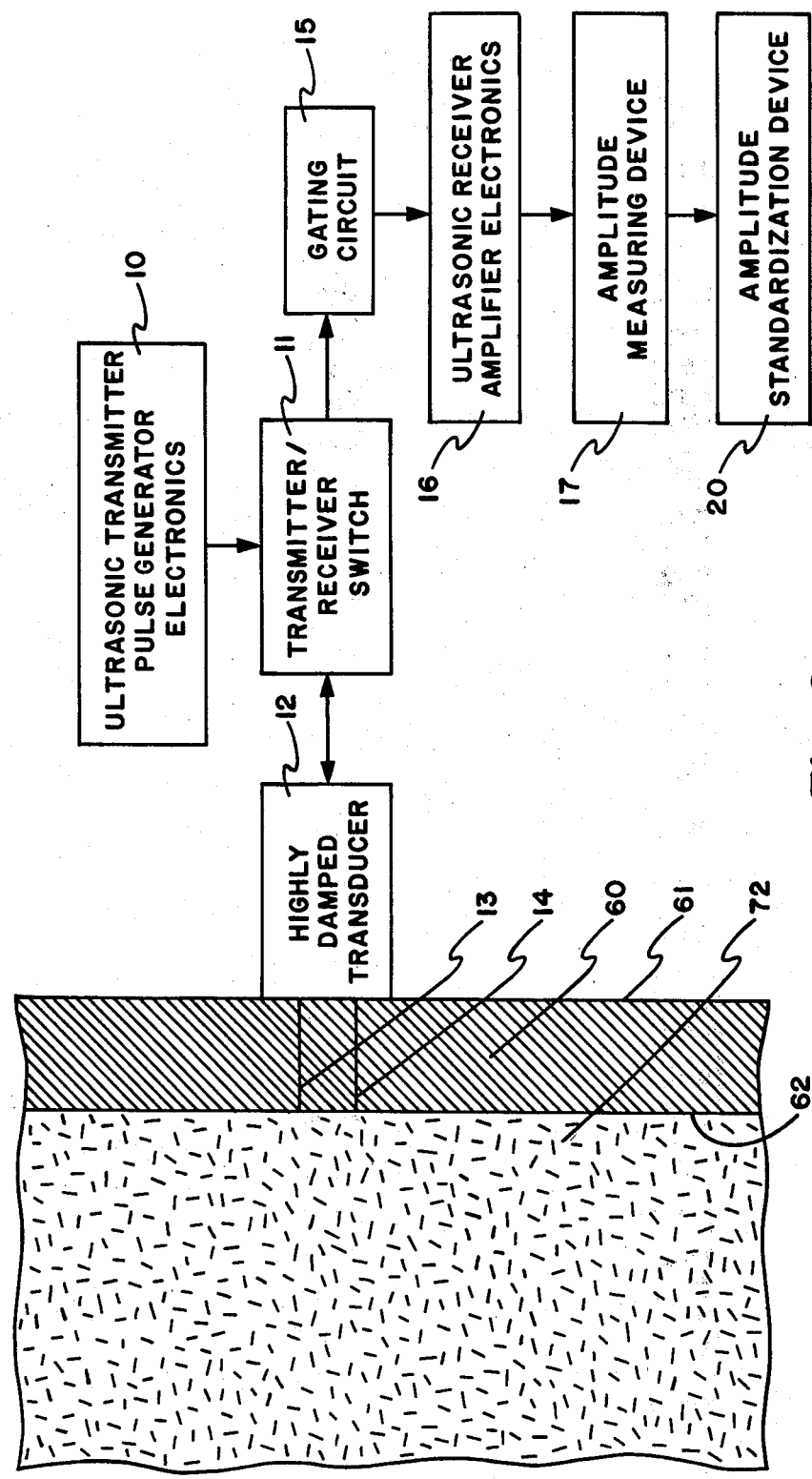
FIG. 2 is a block diagram of the device for measuring the actual value of acoustic characteristic impedance.

FIG. 2 depicts a first extended configuration of the invention of FIG. 1 and is used for a method and device to measure the actual value of acoustic characteristic impedance of a medium 72. FIG. 2 is identical with FIG. 1 except for the addition of an amplitude standardization device 20 which converts the relative acoustic characteristic impedance amplitude value from the amplitude measuring device 17 into an actual value.

The amplitude standardization device 20 is a computer-type device and is preferably a typical electronic circuit, known to those skilled in the art, which has an adjustable gain for amplitude calibration to some standard followed by a transfer function which transfers the amplitude according to the following formula: $W_2 = W_1(K+R)/(K-R)$.

This formula reflects the fact that measurement of the reflected acoustic pulse from the interface of two materials, when the acoustic characteristic impedance of one is known, permits the acoustic characteristic impedance of the unknown material to be determined. In the formula, $W_2$ is the value of the acoustic characteristic impedance of the medium 72 that is to be determined, $W_1$ is the known acoustic characteristic impedance of the reference plate 60, K is the adjusted gain for amplitude calibration, and R is the amplitude of the return signal which may be in phase or out of phase depending on whether the medium 72 is sonically harder or softer than the reference plate 60. For an out of phase return signal, R is expressed as a negative number.

The amplitude gain is set preferably by a previous acoustic characteristic impedance measurement using air as the medium. The acoustic characteristic impedance of air at one atmosphere pressure can be approximated as zero, and thereafter the amplitude gain can be set by adjusting the gain to have the amplitude read one unit (such as one volt) for air. Obviously the amplitude gain could be set, more accurately, using the above formula and a medium with a known exact value of acoustic characteristic impedance.

It should be noted that the acoustic characteristic impedance of the reference plate 60 must be known for this employment of the invention. The operation of the invention configured for the actual acoustic characteristic impedance measurement is the same as that for the relative value, as given above, with the exception that the added amplitude standardization device 20, with the amplitude gain adjusted and the transfer function as given above, will yield the measured value of the acoustic characteristic impedance of the medium 72.

Figure 3:
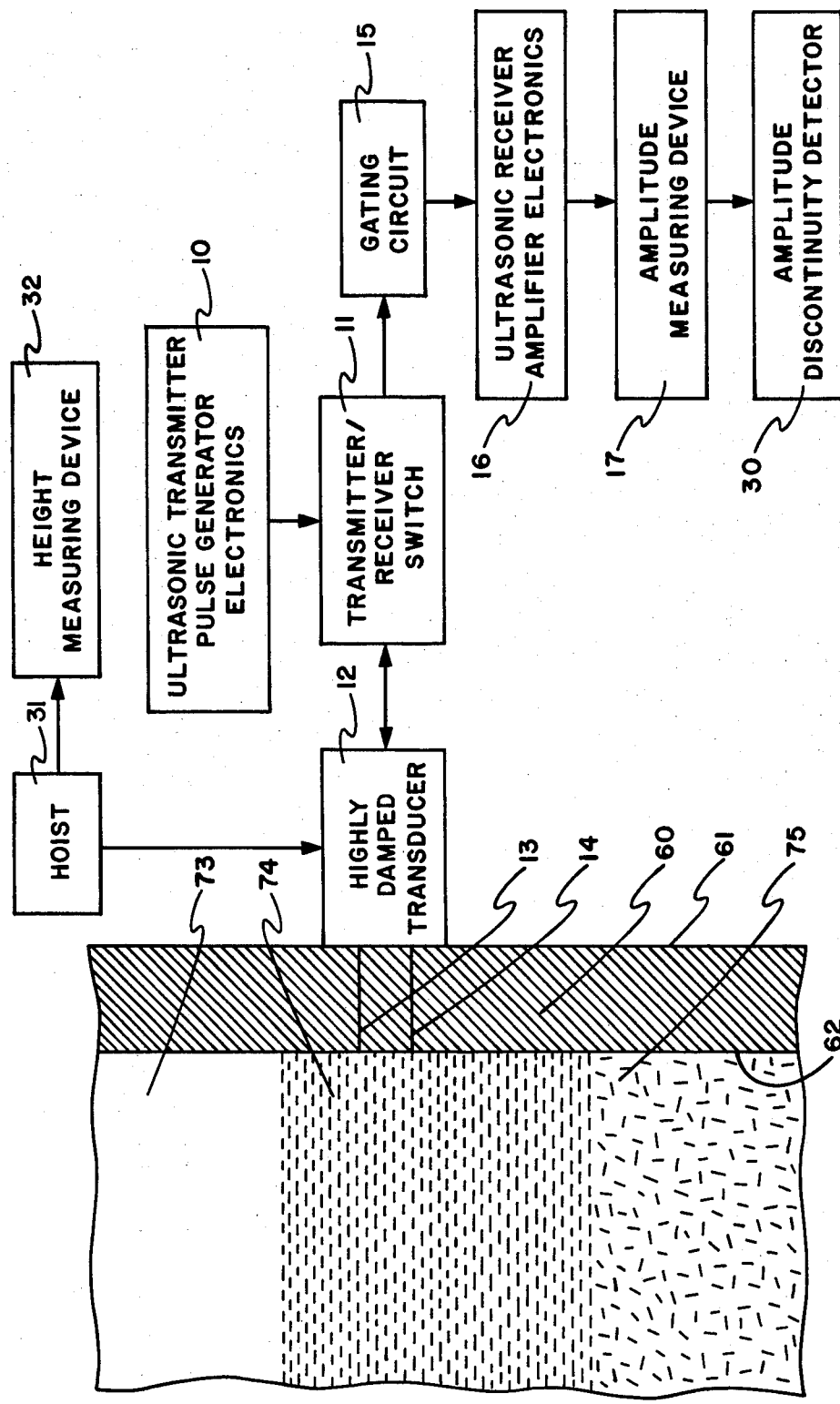
FIG. 3 is a block diagram of the device for locating the interfaces of vertically-layered materials.

FIG. 3 depicts a second extended configuration of the invention of FIG. 1 and is used to measure the interface of vertically-layered materials defining a medium. FIG.

3 is identical with FIG. 1 except for the addition of an amplitude discontinuity detector 30, a hoist 31 or other lifting means, and a height measuring device 32.

The hoist raises and lowers the common transducer 12 of the transmitter and receiver. The height measuring device 32 measures the vertical distance of the transducer 12 from a reference point, and must have an accuracy commensurate with the interface location detection needs. If separate transmitter and receiver transducers are used, the average vertical height of the two transducers would be measured and used to determine the interfaces. Preferably the height measuring device employs circumferential markings on the drum of the hoist to measure the length of hoist cable that has been lowered. Alternatively, the height could be visually observed from distance markings on the hoist cable itself.

The amplitude discontinuity detector 30 indicates differences between successive amplitude measurements. Preferably it is a typical electronic comparison circuit, known to those skilled in the art, set to alarm for a specified difference between successive amplitudes. Alternatively, the discontinuities could be visually observed from a graph of amplitude plotted against vertical height.

The interface locator employment of the invention can be used on the outside of a vessel wall when the reference plate 60 is the tank wall itself. Alternatively, it could be used by lowering a small reference plate, with transducer attached, into a tank containing a liquid and/or gas medium. Additionally it can be used within a drywell inside a tank containing the medium where the wall of the drywell becomes the reference plate.

Interfaces can be detected consisting of any combination of gas/liquid/solid layers, including liquid/liquid, gas/solid, etc. The interface usually has a sharp demarcation between vertically-layered materials, but can be defined to include a gradual interface such as salt having vertical zones of varying degrees of wetness. The interface locator can be used to detect the level of dry salt, wet salt, very wet salt, etc. In this case the discontinuity in amplitude is spread over a greater vertical distance. The technique has been used to determine the level of pumpable interstitial liquid in a buried nuclear waste tank containing salt wastes.

The operation of the interface locator is the same as that for the relative acoustic characteristic impedance configuration of the invention, as given above, with the addition of having repeated measurements of amplitude taken for various vertical heights and then detecting the interface location from the height of the amplitude discontinuity. For example, in going from a gas to liquid, the amplitude will suddenly change at the interface from, for example, a relatively high value to a relatively low value. Obviously, knowledge of possible interfaces present within a vessel makes it easier to detect the nature of the located interface.

The interface locator could obviously be used, with appropriate feedback controls, to control the interface level in a medium, such as the level of a liquid in a tank.

Figure 4:
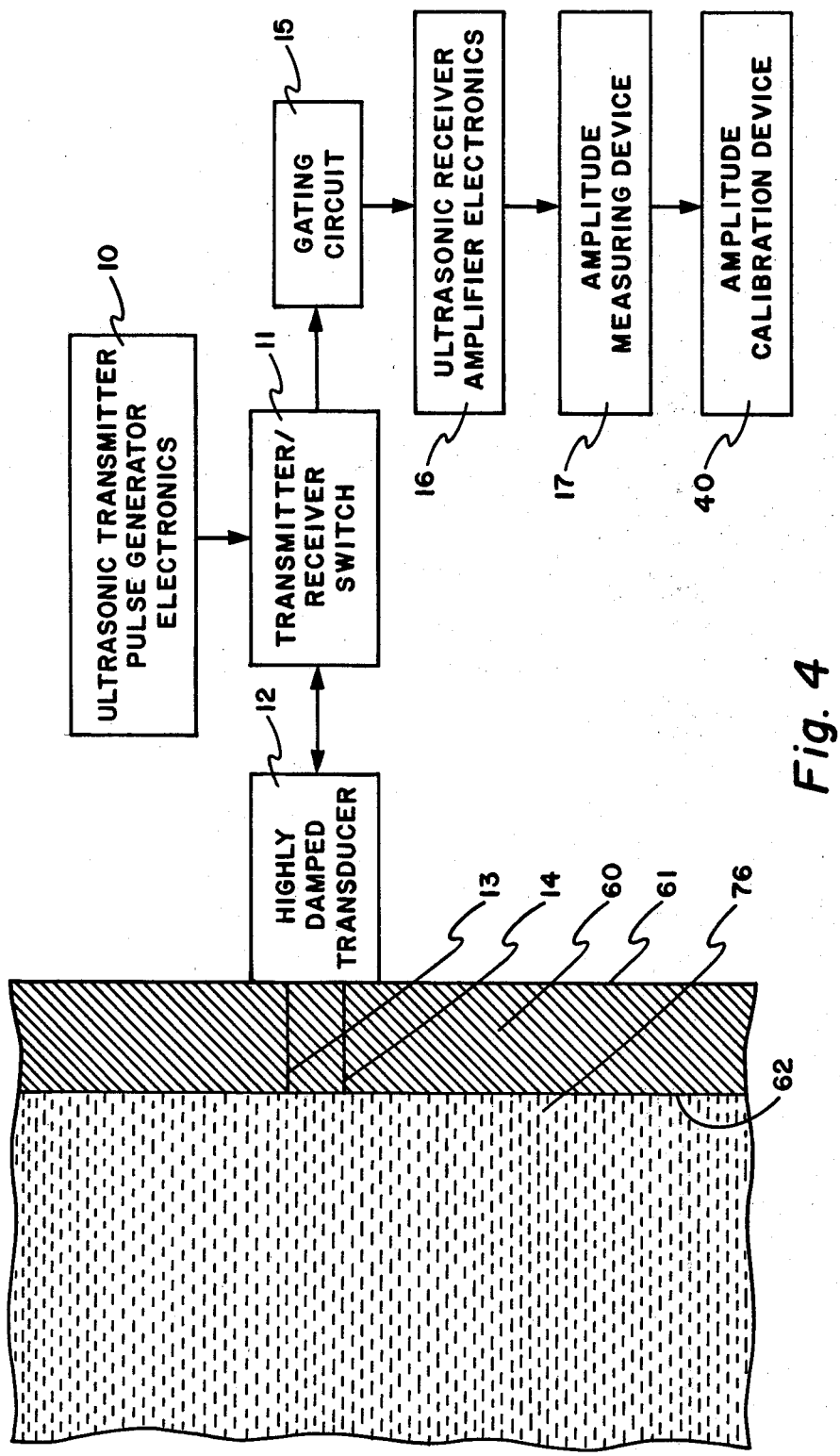
FIG. 4 is a block diagram of the device for measuring the concentration of a first material mixed in a second material.

FIG. 4 depicts a third extended configuration of the invention of FIG. 1 and is used to measure the concentration of a first material mixed in a second material in a medium comprising the two materials. FIG. 4 is identical with FIG. 1 except for the addition of an amplitude calibration device 40 which converts the relative acoustic characteristic impedance amplitude value, from the amplitude measuring device 17, into a concentration measurement.

The amplitude calibration means or device 40 includes preferably a typical electronic circuit, known to those skilled in the art, to calculate and store a list of paired or extrapolated relationships of amplitude and concentration and to match a new value of amplitude with the stored information and output the concentration value. To create the amplitude to concentration relationships, known concentrations of the first material mixed in the second material are tested, and the amplitude of the return signal is measured. The amplitudes and corresponding concentrations are then manipulated to establish the extrapolated or paired relationships and stored.

The operation of the concentration measurer is the same as that of the relative acoustic characteristic impedance measurer, as given above, with the addition of previously calculating and loading the paired relationships as given above, so that the amplitude calibration device 40 will convert the amplitude into the concentration of the medium having the unknown amount of the first material mixed in the second material.

For some mixtures, such as non-electrolytic aqueous solutions (like alcohols and acetone) at certain temperature ranges, the velocity of sound has a clearly defined maximum, and will result in a non-linear acoustic characteristic impedance measurement. Still, use of the acoustic characteristic impedance measurement is practical in the non-electrolytics by considering the following facts and utilizing them in the measurement scheme:

1. There is a critical concentration of a non-electrolytic that is not temperature sensitive regarding adiabatic compressibility and therefore velocity.

2. There is a temperature above which the adiabatic compressibility does not go through a minimum and therefore the velocity does not go through a maximum.

3. The density varies approximately linearly.

Further, the considerations mentioned will allow certain investigations of solutions regarding their molecular physics.

Figure 5:
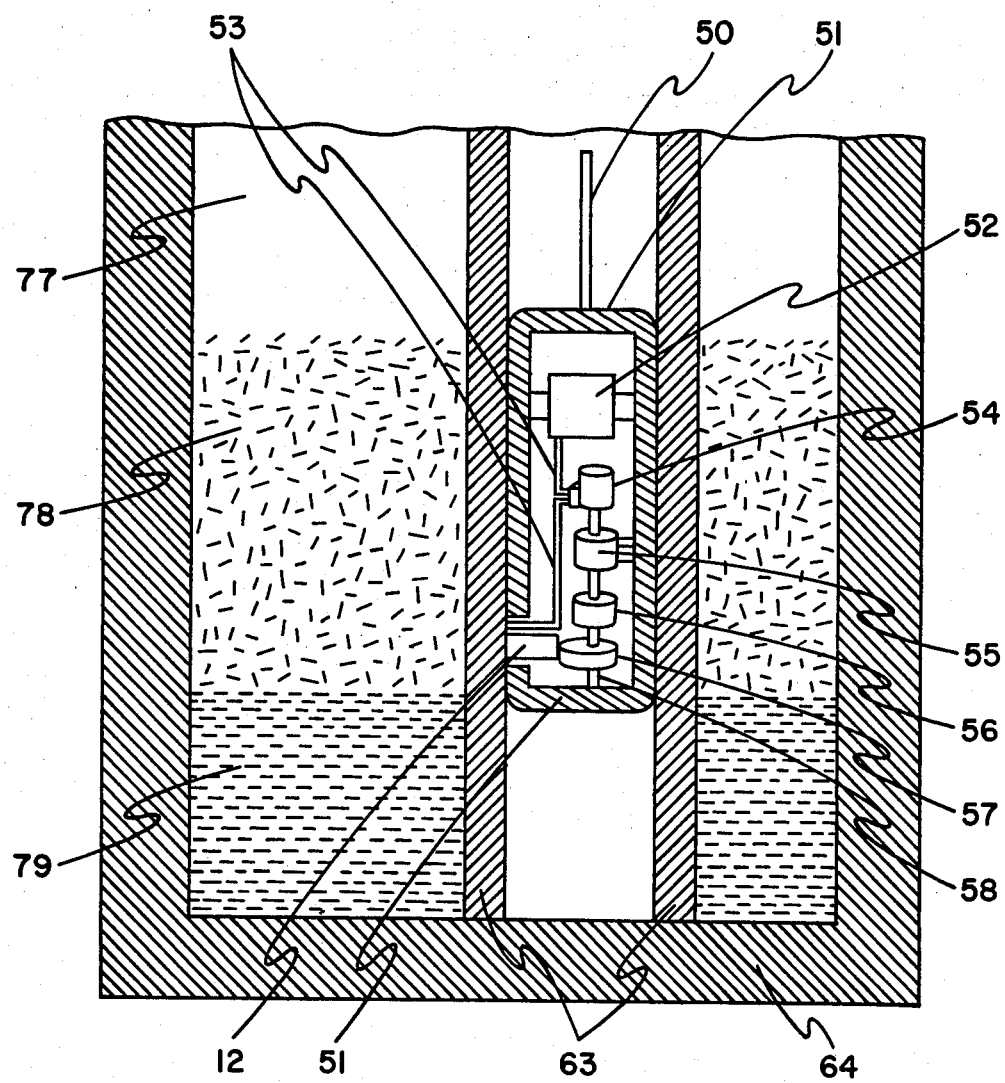
FIG. 5 is a cutaway view of a buried nuclear waste tank, showing how the device of FIG. 3 is employed in a drywell to locate the interstitial liquid level in the nuclear waste.

FIG. 5 depicts the invention employed in a drywell 63 that is placed within a vessel 64 containing vertically-layered gas 77, dry salt 78, and wet salt 79. The invention's electronics have been omitted for clarity and are understood to be connected to the common transmitter-receiver transducer 12 by appropriate wires or transmission cables which would lead outside the housing 51 to the top of the drywell. The housing 51 is raised and lowered by a hoist cable 50. The housing 51 serves to contain the common transducer 12 and put it in acoustic contact with the inner wall of the drywell 63. The simplified mechanics to make the acoustic coupling are shown within the housing 51. A cam 57 moves the transducer 12 into intimate contact with the drywell 63 and it exerts a constant pressure which is provided by a slip clutch 56. A motor 55 drives the cam 57 via the slip clutch 56. The same motor 55 drives a couplant pump 54 which pumps couplant held in a reservoir 52 through flexible tubes 53 to the wall of the drywell 63. A shaft 58 mechanically connects the pump 54, motor 55, slip clutch 56, and cam 57 together. The couplant tubing 53 directs the couplant to the boundary area between the transducer 12 and the drywell 63. The couplant may be a medical acoustic gel or the like.

Figure 6:
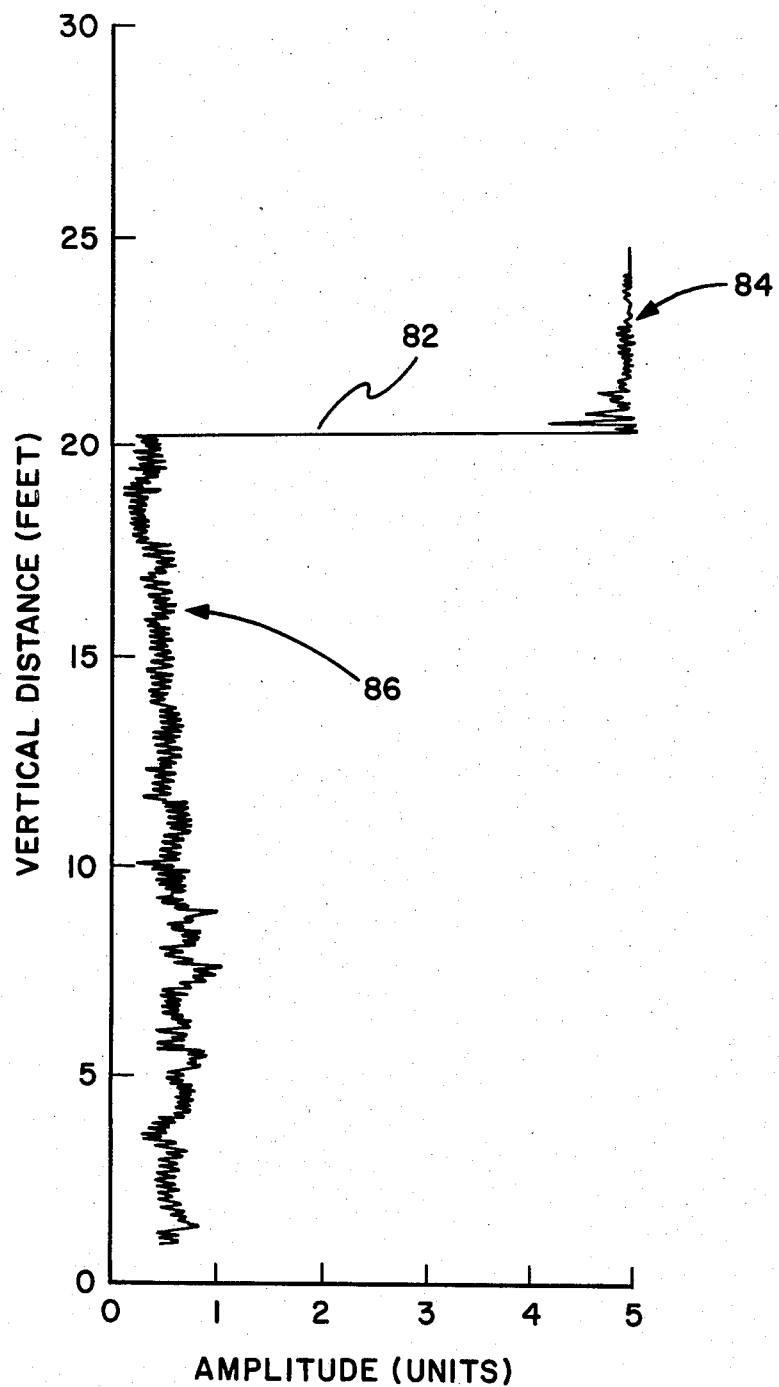
FIG. 6 is a vertical height—amplitude plot showing an amplitude discontinuity which locates a wet salt—air boundary in a nuclear waste tank.

The device shown in FIGS. 3 and 5, when used in a tank partially filled with wet salt, resulted in the graph shown in FIG. 6. This plot for various vertical distances above the tank floor shows the amplitudes of the return pulses. The wet salt/gas interface is the amplitude discontinuity 82 shown just above twenty feet. The amplitude is in arbitrary units with readings of about five indicating air 84 and readings below one indicating wet salt 86.

When the housing 51 is on the bottom of the drywell 63, the motor 55 is caused to operate. This pumps couplant to the space in front of the transducer 12 and starts rotating the cam 57 which moves the transducer 12 into contact with the drywell 63. When an intimate contact between the transducer 12 and the drywell 63 is obtained, the slip clutch 56 slips but maintains constant pressure. As the housing 51 is drawn up the drywell 63 by the hoist cable 50, the motor 55 continues to operate to maintain contact and couplant flow. Also, as the probe is drawn up the drywell 63, the electronics, not shown in FIG. 5, are caused to operate. The repetition frequency of the voltage pulses from the transmitter is such that each successive acoustic pulse from the transducer 12 damps out before a new pulse is generated. This prevents any resonance or standing wave phenomenon from affecting the amplitude reading of the reflected wave.

In summary, by using the amplitude of a return pulse which is the reflection of a highly damped soundwave (usually ultrasonic) transmitted pulse from the boundary between a reference plate and a medium, the interfaces of the medium's materials, if vertically-layered, may be determined. If the medium consists of two mixed materials instead of any number of vertically-layered materials, the amplitude can be compared with a known list or other data and the concentration of the first material mixed in the second material may be calculated. Additionally, if instead of two materials only one material is tested, the amplitude will give the relative acoustic characteristic impedance of that material and, if the acoustic characteristic impedance of the reference plate is known, the value of the acoustic characteristic impedance of the one material may be obtained. The elements of the various configurations of the invention, as shown in the figures, are known to those skilled in the art of ultrasonic nondestructive testing (NDT).

The foregoing description of a preferred embodiment of the invention has been presented for purposes of illustration and description. It is not intended to be exhaustive or to limit the invention in the precise form disclosed, and obviously many modifications and variations are possible in light of the above teaching. The embodiments were chosen and described in order to best explain the principles of the invention and its practical application to thereby enable others skilled in the art to best utilize the invention in various embodiments and with various modifications as are suited to the particular use contemplated. It is intended that the scope of the invention be defined by the claims appended hereto.

I claim:

1. A method of determining the relative acoustic characteristic impedance of a medium, said medium having a gas/solid interface and including an electrolytic aqueous solution, comprising the following steps:
   (a) acoustically contacting a transmitter's highly damped soundwave transducer and a receiver's soundwave transducer with one side of a reference plate by remotely pumping an acoustic couplant between the transducers and the reference plate and then pressing the transducers against the reference plate;
   (b) orienting said transmitter's transducer to transmit a signal to, and said receiver's transducer to receive a reflection of said signal from, the other side of the reference plate;
   (c) physically contacting said other side of said reference plate with said medium;
   (d) sending a highly damped soundwave pulse from said transmitter's transducer into said one side of said reference plate;
   (e) detecting with said receiver's transducer a corresponding soundwave return pulse which is a reflection of said transmitted pulse from the interface between said other side of said reference plate and said medium;
   (f) determining the amplitude of said return pulse, said amplitude indicating the relative acoustic impedance of said medium;
   (g) repeating steps (a) through (f) for various vertical heights in vertically-layered materials defining a medium; and
   (h) determining the discontinuities in the amplitudes, said discontinuities indicating the vertical heights of the interfaces of said vertically-layered materials defining said medium.

2. A device for determining the relative acoustic characteristic impedance of a medium, said medium being vertically layered and having a gas/solid interface and including an electrolytic aqueous solution, comprising:
   (a) a transmitter having a highly damped pulsed soundwave transducer;
   (b) a receiver having a soundwave transducer and an amplifier;
   (c) a reference plate having two sides, one of said sides acoustically contacting said transmitter's transducer and said receiver's transducer, and the other of said sides physically contacting said medium, wherein said reference plate is part of a drywell which is vertically disposed within a tank containing said medium, with said transmitter's transducer oriented to transmit a signal pulse to, and said receiver's transducer oriented to receive a return pulse which is the reflection of said signal pulse from, the interface between said other side of said reference plate and said medium;
   (d) means for remotely pumping acoustical couplant between the transducers and the reference plate;
   (e) means for pressing the transducers against the reference plate;
   (f) electronic gating means for passing substantially only said return pulse to said receiver's amplifier;
   (g) means for determining the amplitude of said return pulse, said amplitude indicating the relative acoustic characteristic impedance of said medium;
   (h) means for vertically displacing said transmitter's transducer and said receiver's transducer;
   (i) means for measuring said vertical displacement; and
   (j) means for determining the discontinuities in the amplitudes for repeated measurements, said discontinuites indicating the vertical heights of the interfaces of said vertical layers.

* * * * *